(12) United States Patent
Erkkila

(10) Patent No.: US 9,433,823 B2
(45) Date of Patent: Sep. 6, 2016

(54) TRAINING APPARATUS FOR GUIDING USER TO IMPROVE FITNESS

(71) Applicant: Polar Electro Oy, Kempele (FI)

(72) Inventor: Mika Erkkila, Oulu (FI)

(73) Assignee: POLAR ELECTRO OY, Kempele (FI)

( * ) Notice: Subject to any disclaimer, the term of this patent is extended or adjusted under 35 U.S.C. 154(b) by 98 days.

(21) Appl. No.: 13/756,767

(22) Filed: Feb. 1, 2013

(65) Prior Publication Data

US 2013/0236868 A1    Sep. 12, 2013

(30) Foreign Application Priority Data

Feb. 3, 2012  (FI) ...................................... 20125122

(51) Int. Cl.
*A63B 69/00* (2006.01)
*A63B 24/00* (2006.01)
*G06F 19/00* (2011.01)

(52) U.S. Cl.
CPC ....... *A63B 24/0062* (2013.01); *G06F 19/3481* (2013.01)

(58) Field of Classification Search
USPC ....................................................... 434/247
See application file for complete search history.

(56) References Cited

U.S. PATENT DOCUMENTS

| 6,601,016 | B1 | 7/2003 | Brown et al. |
| 8,825,445 | B2 * | 9/2014 | Hoffman ............ A63B 24/0062 482/8 |
| 2007/0260482 | A1 | 11/2007 | Nurmela et al. |
| 2008/0086318 | A1 | 4/2008 | Gilley et al. |
| 2011/0281249 | A1 | 11/2011 | Gammell et al. |

FOREIGN PATENT DOCUMENTS

WO        98/40126        9/1998

OTHER PUBLICATIONS

Search Report for Finnish Application No. 20125122, dated Oct. 24, 2012, 2 pages.

* cited by examiner

*Primary Examiner* — Kesha Frisby
(74) *Attorney, Agent, or Firm* — Hoffmann & Baron, LLP

(57) ABSTRACT

A processing system includes a memory storing tasks that define a physical exercise and a target value. The tasks are divided into categories of training requirements, and each category is linked to a progress status indicator. The processing system determines a progress status and retrieves a task from a category corresponding to the progress status; instructs the user to carry out a physical exercise; acquires measurement data generated during physical exercise; compares information acquired from the measurement data with the target value. Upon determining, on the basis of the comparison that the user reached the target value, the processing system stores a task indicator to indicate that the task was completed the progress status of the user has increased sufficiently as a result of completing the task, the processing system raises the progress status of the user, and retrieves a subsequent task.

11 Claims, 5 Drawing Sheets

---

402: DETERMINE TYPE OF AVAILABLE MEASUREMENT DATA

404: SELECT & TASK(S) HAVING TARGET VALUE(S) TO WHICH AVAILABLE MEASUREMENT DATA MAY BE MAPPED

TO 204

TRAINING APPARATUS FOR GUIDING USER TO IMPROVE FITNESS

CROSS-REFERENCE TO RELATED APPLICATION

This application claims priority based on Finnish Application No. 20125122, filed Feb. 3, 2012, which is incorporated herein by reference in its entirety.

BACKGROUND

1. Field

The invention relates to devices configured to monitor, guide, and/or analyse physical training exercise of a person.

2. Description of the Related Art

Personal training devices are used to monitor user's performance during a physical exercise, e.g. a sports activity. Some training devices merely monitor user's physiological properties such as heart rate, activity, acceleration, etc. while other training devices provide the user with instructions as how to carry out the exercise.

SUMMARY

According to another aspect of the present invention, there is provided a processing system processing system comprising at least one memory storing a set of tasks, wherein each task defines a physical exercise and at least one target value for the physical exercise, wherein the tasks are divided into a plurality of categories in an order of increasing training requirements, and wherein each category is linked to a unique progress status indicator representing the training requirements. The processing system further comprises at least one processor. The at least one memory and the at least one processor are configured to cause the processing system to: determine a progress status of a user and retrieve from the memory at least one task from a category associated with a progress status indicator corresponding to said progress status of the user; instruct the user to carry out a physical exercise of a retrieved task; acquire measurement data generated during said physical exercise; compare information acquired from the measurement data with the at least one target value associated with the instructed physical exercise; upon determining on the basis of the comparison that the user has reached at least one target value, store in the memory a task indicator to indicate that the task has been completed; and determine that the progress status of the user has increased sufficiently as a result completing the task, raise the progress status of the user, and retrieve a subsequent task from a category associated with a higher training requirements.

Embodiments of the invention are defined in the dependent claims.

BRIEF DESCRIPTION OF THE DRAWINGS

Embodiments of the present invention are described below, by way of example only, with reference to the accompanying drawings, in which.

DETAILED DESCRIPTION

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Figure 1:
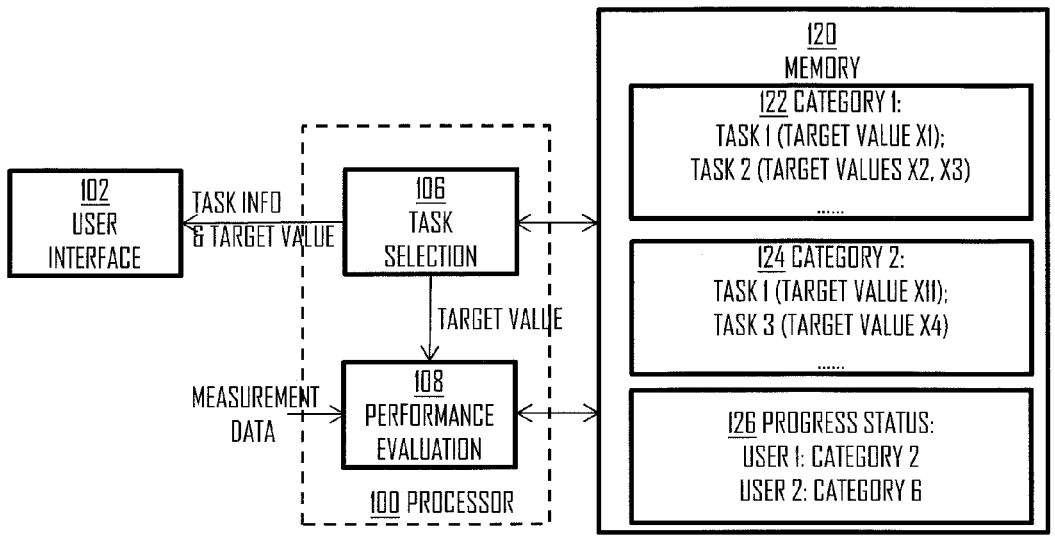
FIG. 1 illustrates a training guidance apparatus according to an embodiment of the invention.

FIG. 1 illustrates an apparatus according to an embodiment of the invention. The apparatus comprises at least one memory 120 storing a set of tasks. Each task defines a physical exercise and at least one target value for the physical exercise. The tasks are divided into a plurality of categories 122, 124 in an order of increasing training requirements, and each category is denoted by a unique progress status indicator representing the training requirements. The training requirements may represent the training difficulty to indicate how demanding the tasks of the category are for the user. The at least one memory 120 may additionally store a computer program comprising program code instructions configuring the apparatus to process the information contained in the at least one memory 120. The apparatus further comprises at least one processor 100 or processing circuitry configured to execute the computer program, thus configuring the apparatus to execute a process for guiding and monitoring physical exercises carried out by a user of the apparatus. An embodiment of the process is described now with reference to a flow diagram of FIG. 2.

Figure 2:
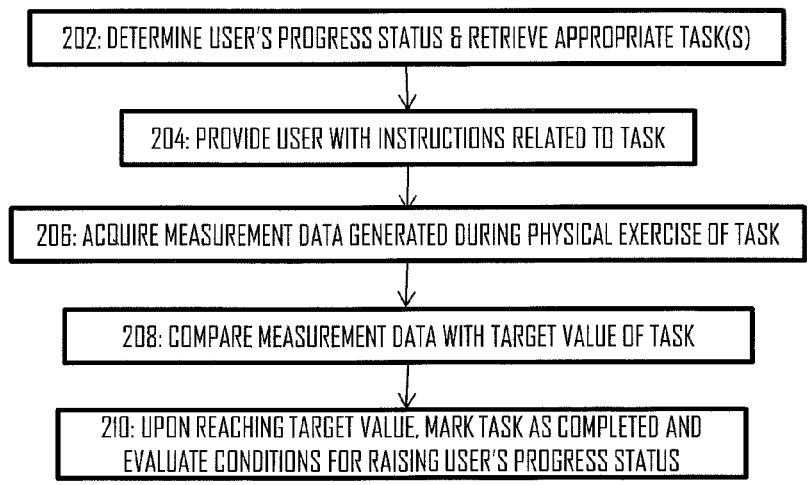
FIG. 2 illustrates a flow diagram of a process for selecting and monitoring execution of tasks in the training guidance apparatus.

Referring to FIG. 2, the process comprises determining a progress status of the user and retrieving from the memory at least one task from a category 122, 124 associated with said progress status (block 202). Block 202 may be carried out by a task selection module 106 which may be comprised as a sub-circuitry in the processor 100, or it may be understood as a computer routine executed by the processor 100. The progress status of the user may be determined be reading the user's current progress status indicator from the memory 120, wherein the progress status indicator indicates the category from which the tasks should be retrieved. The memory 120 may store a record 126 comprising progress status indicators of the users of the apparatus. The progress status indicators may be as linked to a user identifier, e.g. a name. The task selection module 106 may retrieve the appropriate user's progress status indicator upon the user is authenticated through user input, for example. The task selection and retrieval may comprise retrieval of the target value(s) associated with the task(s). In block 204, the task selection module 106 outputs information on the retrieved task(s) to the user through a user interface 102. In an embodiment, the user interface 102 is comprised in the apparatus, e.g. in the same casing with the processor 100 and the memory 120. In another embodiment, the user interface is comprised in another apparatus, and a connection between the processor 100 and the user interface 102 may be realized by a wired or wireless connection. The apparatus and the user interface apparatus may comprise appropriate communication circuitries to realize the wired or wireless connection, as known in the art. The information on the selected task(s) may comprise instructions instructing the user to carry out a physical exercise of the retrieved task(s). The information presented to the user may also comprise the retrieved target value(s) for the physical exercise.

After block 204, the start of the physical exercise may be triggered. Triggering the start of the physical exercise may cause the process to proceed to block 206. In block 206, a performance evaluation module 108 of the processor 100 acquires measurement data generated during said physical exercise. The measurement data may be originated from at least one sensor measuring any property related to the physical exercise. The sensor may be comprised in the apparatus, or the sensor may be physically separate from the apparatus. In the latter embodiment, a connection between the processor 100 and the sensor may be realized by a wired or wireless connection. The apparatus and the sensor may comprise appropriate communication circuitries to realize the wired or wireless connection, as known in the art.

Upon acquiring the measurement data, the performance evaluation module 108 may process the measurement data into a form that corresponds to the form in which the target value(s) is/are presented in the apparatus and, then in block 208, compare the measurement data with the target value(s) associated with the on-going physical exercise. Block 208 may be carried out during the exercise. Upon determining on the basis of the comparison that the user has reached the at least one target value (block 210), the performance evaluation module 108 stores in the memory 120 a task indicator to indicate that the task has been completed. When the task is associated with a plurality of target values, block 210 may comprise determining that all the target values of the task shall be reached before the task is considered to be completed. After the task has been completed, the performance evaluation module 108 determines whether or not a progress status of a user has increased sufficiently as a result completing the task. If so, the performance evaluation module 108 may raise the progress status of the user and update the user's progress status indicator in the memory 120. As a consequence, the task selection module 106 retrieves a subsequent task from a category associated with higher training requirements.

Figure 3:
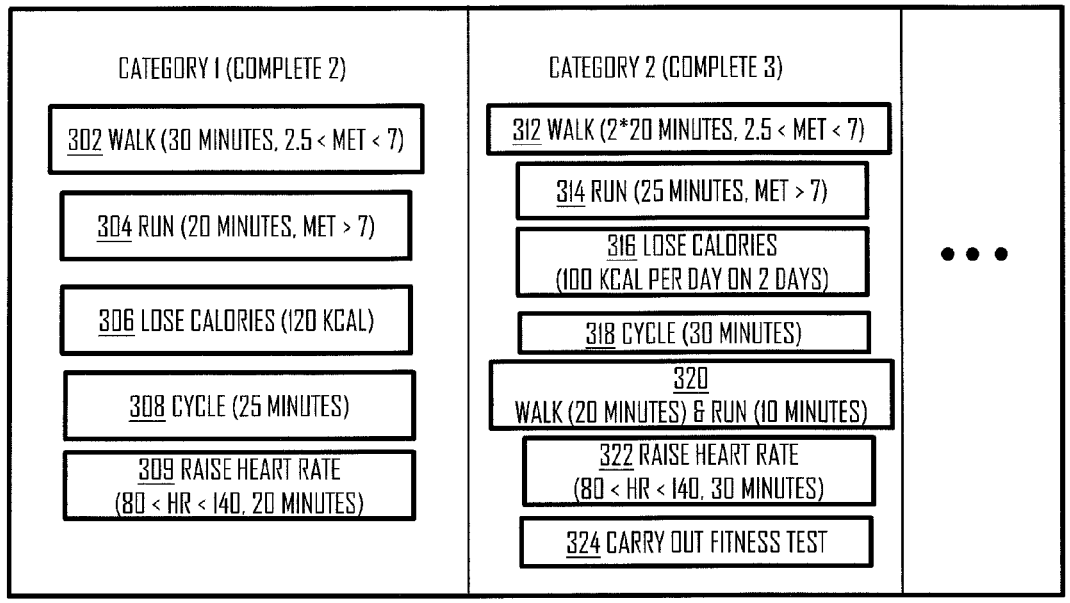
FIG. 3 illustrates an embodiment of a database storing at least some of the tasks used in the training guidance.

Now, let us consider some embodiments of the tasks and associated target values with reference to an embodiment of a database illustrated in FIG. 3. The database may be stored in the memory 120. As already described, the database may store the tasks as categorized according to their training requirements represented by the progress status indicator of each category. FIG. 3 illustrates only two categories, but it should be appreciated that the number of categories may be arbitrary. Additionally, the increase in the training requirements between the consecutive categories may be realized through a number of ways, some of which are described below.

Referring to FIG. 3, a task may define an exercise or activity type such as walking (tasks 302, 312), running (tasks 304, 314), cycling (tasks 308, 318), swimming, ski-ing, roller-skating, etc. The task may also define some minimum boundaries for the exercise type that may be derived from the target value(s) associated with the task, e.g. running for 20 minutes (task 304). In another example, the task may define only the boundaries and let the user to decide how to meet the boundaries, e.g. tasks 306, 316, 309, and 322 that define tasks where the user needs to expend a determined amount of energy (tasks 306, 316) or raise the heart rate for a determined time period (tasks 309, 322). The measurement data for tasks 302 to 306 and 312 to 316 may be acquired from an activity sensor arranged to measure energy expenditure rate which may characterized in absolute scale in calorie or Joule unit per time unit, such as minute. The activity may also be expressed in or MET (Metabolic Equivalent of Task) unit The MET is a physiological measure expressing the energy cost of physical activities, and it is defined as a ratio of metabolic rate during the physical activity to a reference metabolic rate. The reference metabolic rate may be derived from physical properties of the user, e.g. age, gender, weight. Typically, MET=1 when the user sits quietly and a higher MET indicates higher activity. In an embodiment, the MET may vary between 0.9 (sleeping) to 18 (running at a very high speed, e.g. 17.5 kilometres per hour, km/h). With reference to task 302, the target values of the task may be set such that the measure MET of the user has to be between 2.5 and 7 for the duration of 30 minutes to complete the task. MET value 3.3 represents walking at 4.8 km/h. With reference to task 304, the target values of the task may be set such that the measure MET of the user has to be over 7 for the duration of 20 minutes to complete the task. The MET may be mapped directly to the calorie consumption of task 306. Alternatively, tasks 302 and 304 may define speed limits for running and walking, and the measurement data may be speed data acquired from a speed sensor or a positioning device.

The measurement data for the tasks 309, 322 may be acquired from a heart rate sensor attached to the user to measure the heart rate of the user. The task may specify as the target values the target heart rate or a heart rate range for the task and a duration the heart rate shall be maintained within the target heart rate (range), and the performance evaluation module 108 may be configured to monitor the heart rate data acquired from the heart rate sensor so as to determine whether or not the heart rate is maintained in the specified range for the specified duration to complete the task.

In an embodiment, at least some of the tasks may define a plurality of physical exercises separated from each other. The separation may be realized by the activity type (task 320) such that the task instructs the user to carry out two physical exercises of different activity type, e.g. walking and running as in task 320. Another example of the separation is time-based separation such that the two physical exercises are carried out discontinuously, e.g. on different days (task 316).

In an embodiment, the task defines a physical exercise in which the user is instructed to perform an activity, and the target value may be set such that the user has to move to reach the target value. In another embodiment, the task defines a physical exercise in which the user is instructed to rest and the target value may be set such that the user has to remain at rest to reach the target value, e.g. MET<1.5.

Table 1 below lists examples of tasks at different categories and examples of target values that may be used in connection with each task. Note that X is used as a variable in connection with many tasks and that may have a different value for each task.

TABLE 1

| Task | Target value |
|---|---|
| Be active X minutes | MET > 2.0 for X min |
| Walk X minutes | 2.5 < MET < 7.0 for X minutes |
| Walk X kilometres (km) | 2.5 < MET < 7.0 for X km |
| Walk X paces | X paces |
| Walk X paces in Y minutes | X paces in Y minutes |
| Run X minutes | MET > 7.0 for X minutes |
| Run X km | MET > 7.0 for X km |
| Energy expenditure | X calories |
| Raise heart rate (HR) to at least X for Y minutes | HR > X for Y minutes |
| Complete a training program with heart rate zones | HR1 < HR < HR2 for at least Y1 min: HR3 < HR < HR4 for at least for Y2 min |
| Obtain required training load TL | TLmin < TL < TLmax |
| Run X minutes with Y < HR < Z | Y < HR < Z for X minutes |
| Run X km with Y < HR < Z | Y < HR < Z for X km |
| Be active X minutes with Y < HR < Z | with Y < HR < Z for X minutes |
| Run X minutes with Y < HR < Z and speed at least S km/h | Y < HR < Z for X minutes and speed > S km/h for X minutes |
| Run X km with Y < HR < Z and speed at least S km/h | Y < HR < Z for X km and speed > S km/h for X minutes |
| Carry out fitness test (324 in FIG. 3) | Fitness test activated and executed in the apparatus |
| Ski X minutes | Skiing activity detected for X minutes |
| Cycle X minutes | Cycling activity detected for X minutes |
| Play tennis for X minutes | Tennis activity detected for X minutes |
| Rest for X minutes/hours/days | MET < X for X minutes/hours/days |

As shown in Table 1 and FIG. 3, the tasks may define various physical exercises and embodiments of associated target values that may be used to measure the completion of the exercise. The target values may be measured with sensors related to the exercise, e.g. the energy expenditure rate may be measured with an activity sensor comprising at least one accelerometer or with a heart rate monitor, the paces may be measured with a pedometer, the heart rate may be monitored with a heart rate sensor, the time may be measured with a clock, the speed may be measured with a speed sensor or positioning device, the execution of the fitness test may be detected by the user activating the fitness test in the apparatus of FIG. 1 and the completion of the fitness test, cycling rate may be measured with a cadence sensor, the sports type may be detected by using at least on accelerometer attached to the user and configured to measure the motion of the user's body and compare acceleration signals so measured with reference signals typical to each sports type, and calorie expenditure may be measured with numerous sensors, as known in the art. The above-mentioned fitness test may be a Polar fitness test as described in U.S. Pat. No. 6,277,080 in which the fitness or exertion endurance is measured from heartbeat at rest. The fitness test may comprise a cardiovascular fitness test, a strength fitness test, a flexibility test, a brain fitness test or an endurance fitness test, for example.

As mentioned above, the training requirements may be raised as the progress status is raised. The training requirements may be increased by increasing the duration, distance, heart rate, energy expenditure, etc. of the exercise. In another embodiment, the training requirements are increased by requiring the repetition of an exercise of a lower progress status by an increased number of times. In another embodiment, the training requirements are increased by reducing the time in which the user has to carry out the same exercise, e.g. run X km in shorter time. In yet another embodiment, the training requirements are increased by increasing the number of exercises in a single task. In yet another embodiment, the training requirements are increased by providing long-term tasks, e.g. tasks that define physical exercises which span over a higher duration in time, e.g. over days or weeks and which must be carried out discontinuously. In yet another embodiment the training requirements are increased by increasing the number of tasks that must be completed before the progress status may be increased. As shown in FIG. 3, the user has to complete two tasks on category one to advance to category two, and the user has to complete three tasks on category two to advance to category three. The numbers are obviously merely examples and no limiting this embodiment.

Figure 4:
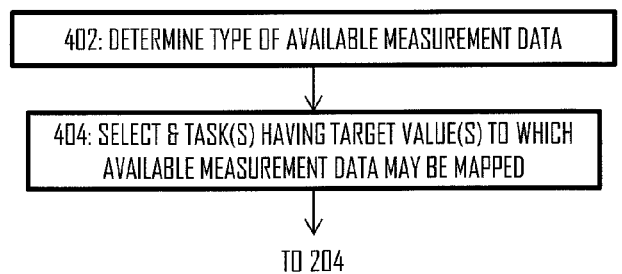
FIG. 4 illustrates a flow diagram of an embodiment for limiting the number of available tasks.

In an embodiment, the task selection module 106 is configured to determine what type of measurement data is available to the apparatus and, then, select the task(s) accordingly. For example, the task selection module may select a task having a target value that is compatible with the available measurement data and rule out task that to which no valid measurement data is available. FIG. 4 illustrates a flow diagram of such a process. This process may be executed as a sub-routine of block 202. Referring to FIG. 4, the task selection module 106 determines in block 402 what type of measurement data will be available to the apparatus during the physical exercise. In an embodiment, this determination is made by determining the available sensors. The memory may also store information on the sensor(s) that should be connected to the apparatus so as to allow execution of each task. As a consequence, the task selection module is able to determine a subset of tasks that may be selected on the basis of the knowledge about the sensors currently connected to the apparatus. In block 404, the task selection module 106 selects the task or tasks to be retrieved from the memory such that the selected task or tasks match with the type of measurement data the apparatus is able to acquire. This embodiment allows the apparatus to rule out those tasks that cannot be currently measured. Therefore, the apparatus does not present to the user such tasks that cannot be completed.

Figure 5:
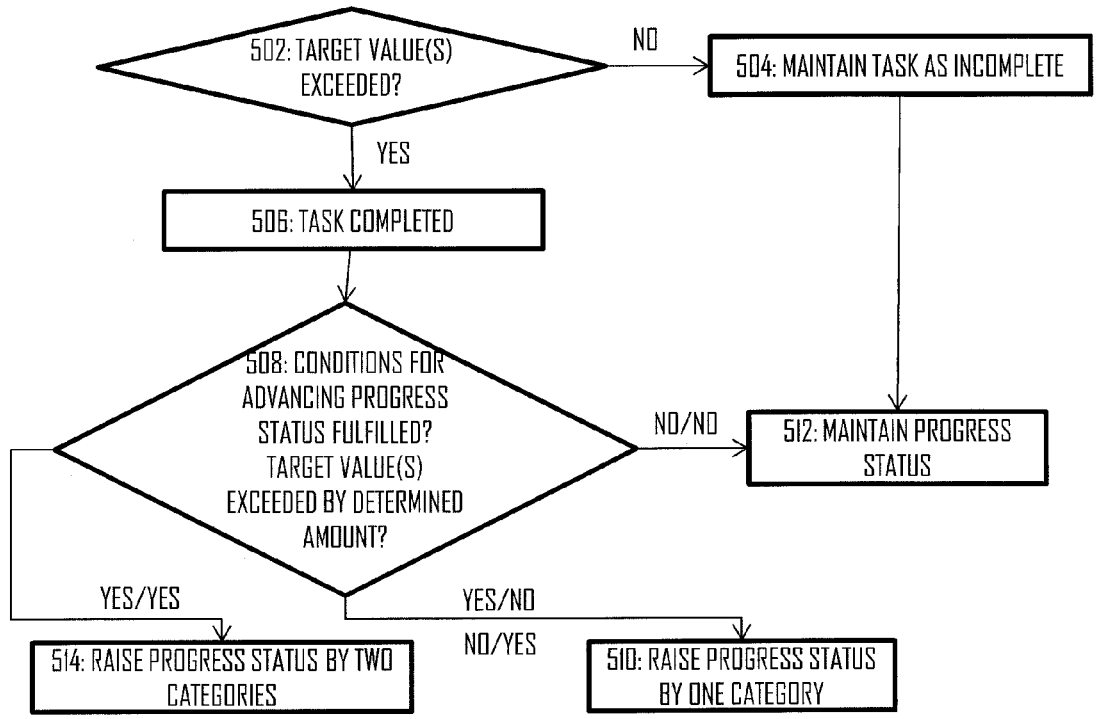
FIG. 5 illustrates an embodiment for determining whether or not to raise a user's progress status in the apparatus.

Let us now consider an embodiment for updating the progress status of the user on the basis of completion of a task with reference to a flow diagram of FIG. 5. FIG. 5 may be understood as an embodiment of block 210. The process of FIG. 5 may be carried out by the performance evaluation module 108. Referring to FIG. 5, the performance evaluation module determines in block 502 whether or not the target value(s) of the currently performed task have been reached at the end of the task. The end of the task may be determined by expiry of a time limit of the task or upon user input indicating the end of the task. If in block 502 it is determined that the target value(s) has/have not been reached, the process proceeds to block 504 in which the task is considered as incomplete and a status of the task is maintained as "not completed". As a consequence, the progress status of the user is maintained (block 512). On the other hand, if the target value(s) have been reached such that the measurement data indicates that conditions for completing the task have been fulfilled, the process proceeds from block 502 to block 506 in which the task is marked as completed in the memory 120. Thereafter, the process proceeds to block 508 in which it is determined whether or not the conditions for increasing the progress status have been fulfilled in terms of a number of completed tasks in the current category. As described above in connection with FIG. 3, the database may store information on the number of tasks that must be completed to achieve the increase in the progress status. Block 508 may also comprise determining whether or not the target value(s) of the recently completed task have been exceeded by a determined amount, e.g. by a determined percentage (e.g. 30%). The determined amount may be set separately for each category, or the same amount may be applied to a plurality of categories or even to all categories. If the mere completion of the task does not yet qualify for the increase of the progress status, e.g. the number of completed tasks is still below the number of completed tasks that qualifies for the increase in the progress status and advance to the higher category, and if the task was completed such that the target value(s) was/were not exceeded by the determined amount, the process proceeds to block 512 in which the current progress status is maintained.

If the number of completed tasks qualifying for the increase in the progress status have been fulfilled and if the task was completed such that the target value(s) was/were not exceeded by the determined amount, the process proceeds from block 508 to block 510 in which the progress status is raised by one to the next category. If the number of completed tasks qualifying for the raise of the progress status have been fulfilled and if the task was completed such that the target value(s) was/were exceeded by the determined amount, the process proceeds to block 514 in which the progress status is raised by at least two categories.

In general, the user may achieve the increase in the progress status by completing the tasks according to the requested conditions defined by the target values or by excelling in the completion of a task, or both. Excelling in the completion of the task may mean that the user exceeds the required minimum requirements by the determined amount, and this may be measured by using the measurement data. In an embodiment, excelling in the completion of one task alone may qualify for the increase by a plurality of categories.

In another embodiment, excelling in a given task may result in that the apparatus is configured to lower the target value(s) of a subsequent task as a reward to the user. In another embodiment, the reward may be a one-time prevention of decrease in the progress status when the decrease is triggered the next time (see the description related to the decrease of the progress status below). In yet another embodiment, the reward is that the user may carry out an arbitrary physical exercise, e.g. one not selected by the task selection module, so as to have one task completed on the current category.

Figure 6:
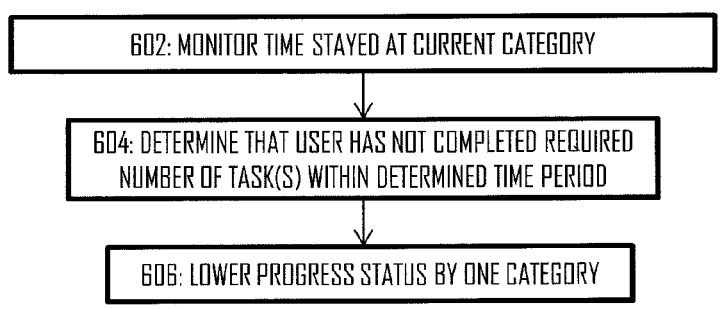
FIG. 6 illustrates an embodiment for determining whether or not to decrease the user's progress status in the apparatus.

The performance evaluation module 108 may also be configured to decrease the progress status if determined conditions for the decrease have been fulfilled. One criterion for decreasing the progress status may be time. FIG. 6 illustrates an embodiment of a flow diagram relating to a process for considering the decrease of the progress status of the user. The process may be carried out by the performance evaluation module 108. Referring to FIG. 6, the performance evaluation module 108 monitors in block 602 the time the user has been maintained on the current category. This may be realized by launching a timer in connection with increase in the progress status, wherein the timer counts a determined period of time. In block 604, it is determined that the user has not completed a required number of tasks within a determined time period. The time period may be the time period counted by the timer, and block 604 may be triggered by the expiry of the timer. As a consequence, the process proceeds to block 606 in which the progress status of the user is decreased by one category meaning that the user is next provided with tasks that have lower training requirements. In an embodiment, the time period counted by the timer may be set to a different value on different categories. This may be used as one embodiment for increasing the training requirements, wherein the user has to complete the required number of tasks faster. On the other hand, if the higher categories require completion of more tasks or tasks that span over a large time period, the time period counted by the timer may be extended accordingly. Therefore, the skilled person will select the time period according to tasks and the overall training requirements of each category.

Another embodiment for decreasing the progress status is a determined number of failed tasks. Each category may comprise a number of tasks that the user must not fail, or the progress status is decreased. For example, the performance evaluation module 108 may decrease the progress status when the user has started but failed to complete a determined number of tasks.

In an embodiment, the apparatus may allow the user to prevent a decrease in the progress status because of a sickness, for example. The apparatus may be configured to stop the timer counting the period of time stayed at the current category upon receiving an appropriate user input. The user input may be a selection of a user interface component denoted by "sick leave" or "injury" and displayed to the user through the user interface 102. This functionality may be applied to the tasks as well, e.g. a task that spans over a large period of time (e.g. days or weeks) and that also specifies a time limit in which the task must be completed may be put on hold in this manner.

Figure 7:
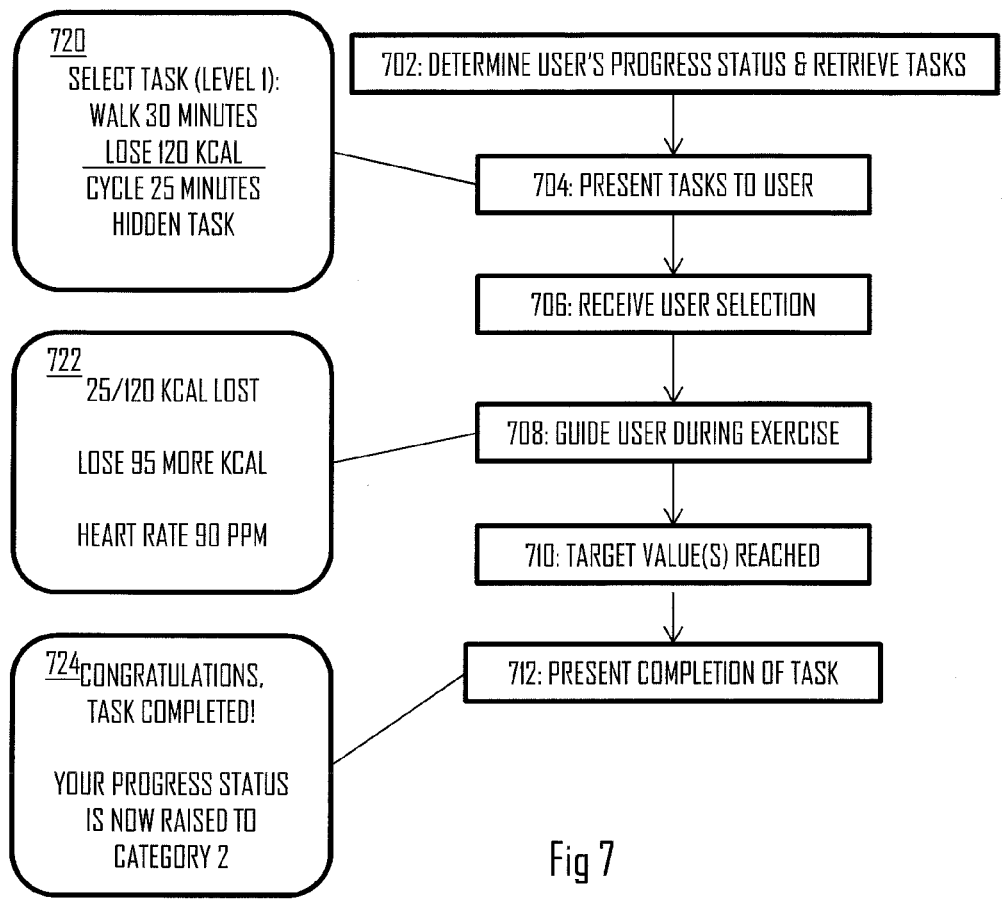
FIG. 7 illustrates yet another embodiment for guiding training of the user and presenting relevant information to the user.

FIG. 7 illustrates a detailed flow diagram of the process for guiding the user to carry out the tasks in connection with examples of information that may be displayed to the user through a display unit of the user interface 102. Referring to FIG. 7, the task selection module 102 determines the user's progress status and, in some embodiments, other parameters affecting the selection of the tasks (e.g. the available measurement data) and retrieves a plurality of tasks from the memory unit. The tasks may be selected in two phases: first according to the above-mentioned criteria and then a subset of remaining tasks may be selected according to another criterion, e.g. randomly or by selecting tasks relating to physical exercise types that the user did not carry out on the previous category. This improves the versatility of the physical tasks the user is required to perform. Upon selecting the subset of tasks in block 702, the task selection module 106 may present the selected tasks to the user through the user interface (display 720 in FIG. 7) in the form of a list, for example. The user may then select, by using an input device and a cursor displayed in the display 720, a task the user wishes to carry out at the moment. The task selection module 106 receives the user input in block 706 and launches the task selected by the user. The task selection module may also activate the appropriate sensor(s) needed to measure the appropriate measurement data for the task. The launch may comprise providing the user with instructions as how to complete the physical exercise(s) of the task. The user is guided through the physical exercise and the task in block 708 in which the apparatus provides appropriate information on the display 722. The information presented to the user may comprise a portion of the task that the user has already completed or accumulated, e.g. the energy expended since the start of the exercise as shown in display 722. The information presented to the user may comprise a portion of the task that still has to be completed or accumulated, e.g. the amount of calories the user still has to lose to complete the task as shown in display 722. The information presented to the user may comprise other information related to the task, e.g. the heart rate and/or the speed.

In block 710, it is determined that one, more than one, or all the target values of the exercise has/have been reached. This may be determined by the performance evaluation module 108 as a result of monitoring the execution of the task. As a consequence, the performance evaluation module 108 may present to the user an indication of the completion of the task in block 712 (display 724). If the completion of the task qualifies for the increase in the progress status, that may also be displayed to the user.

Referring to the list of tasks presented to the user (display 720 in FIG. 7), the list may comprise tasks whose physical exercise(s) are presented to the user (walk, lose calories, and cycle). In an embodiment, the task selection module may also be configured to present to the user at least one task whose contents are not presented to the user before the user has selected the task (hidden task in display 720). This "mystery task" may have the same contents and target value(s) than an arbitrary other task on the same category, or it may be a unique task. In any case, the apparatus is configured to present the instructions and the target values of the mystery task to the user only after the task has been selected to be carried out. This mystery task may have higher training requirements than other tasks on the same category, but the reward may also be higher, e.g. completing the mystery task may equal to the completion of a plurality of conventional tasks. In an embodiment, the task selection module presents only one mystery task per category at a time, but the contents of the mystery task may vary. The task selection module 106 may be configured to present mystery tasks starting at a determined category above the lowest category, e.g. starting from category 10 upwards.

Figure 8:
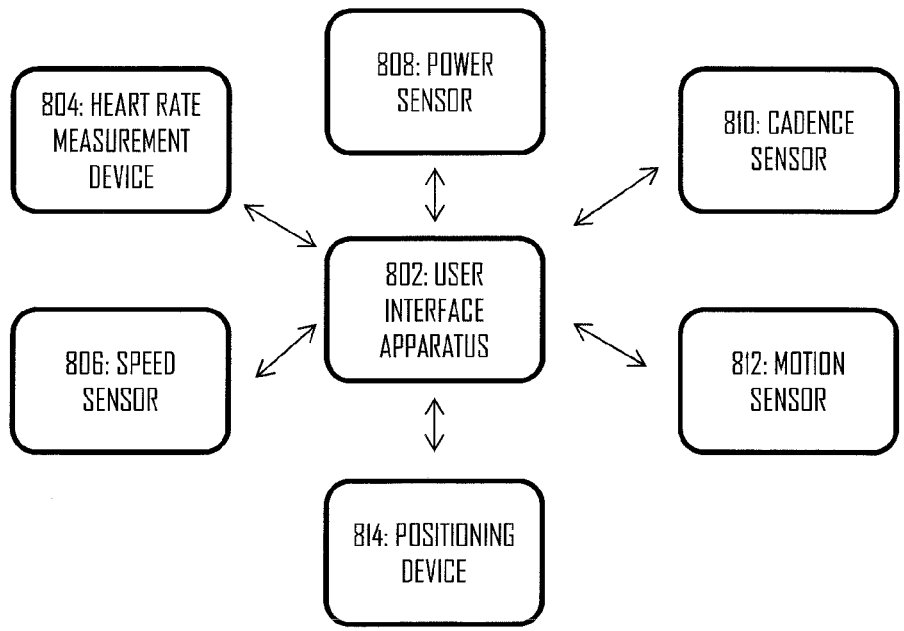
FIGS. 8 and 9 illustrate embodiments of a processing system used for training guidance.
Figure 9:
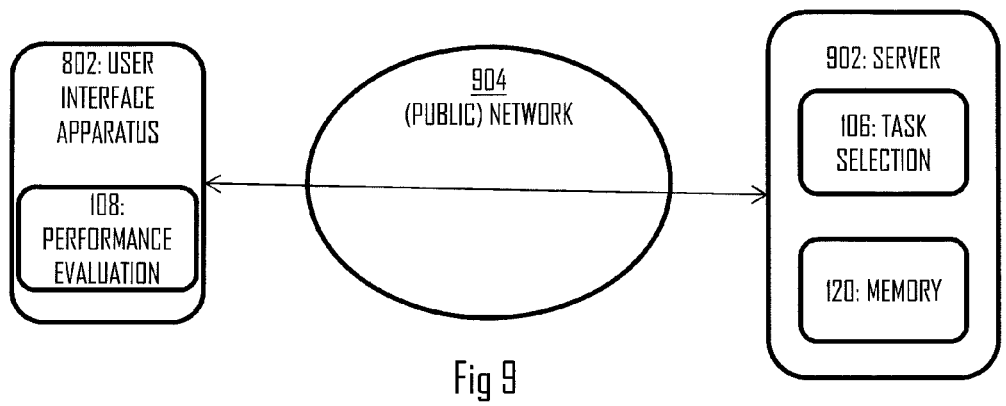

Let us now consider some embodiments of the apparatus according to the invention with reference to FIGS. 8 and 9. FIG. 8 illustrates an embodiment in which the apparatus of FIG. 1 is comprised in a user interface apparatus 802, e.g. a personal electronic device of the user.

In an embodiment, the interface apparatus is a portable electronic device carried by the user.

In an embodiment, the user interface apparatus is a wrist device. In an embodiment, the user interface apparatus is a mobile phone, such as a smart phone.

In an embodiment, the user interface apparatus is a tablet computer, such as iPad.

In an embodiment, the user interface apparatus is a device attached to exercise equipment used by the user, e.g. a bicycle or a treadmill.

In an embodiment, user interface apparatus 802 comprises the memory 120 and the processor 100 comprising the task selection module 106 and the performance evaluation module 108 in the same casing. The user interface apparatus 802 may establish a wired or wireless connection to at least one of the following sensor devices: a heart rate measurement device 804, a speed sensor 806, a pedaling power sensor 808, a cadence sensor 810, a motion sensor or an activity sensor 812, and a positioning device 814.

In an embodiment, the user interface apparatus 802 may be integrated into any one of the above-mentioned sensors. The wired connection may be a Universal Serial Bus connection or a vendor-specific wired connection, for example. The wireless connection may be based on Bluetooth, Bluetooth low energy, magnetic induction, Zigbee, IEEE 802.11, or ANT by Dynastream Innovations Inc., for example.

Figure 10:
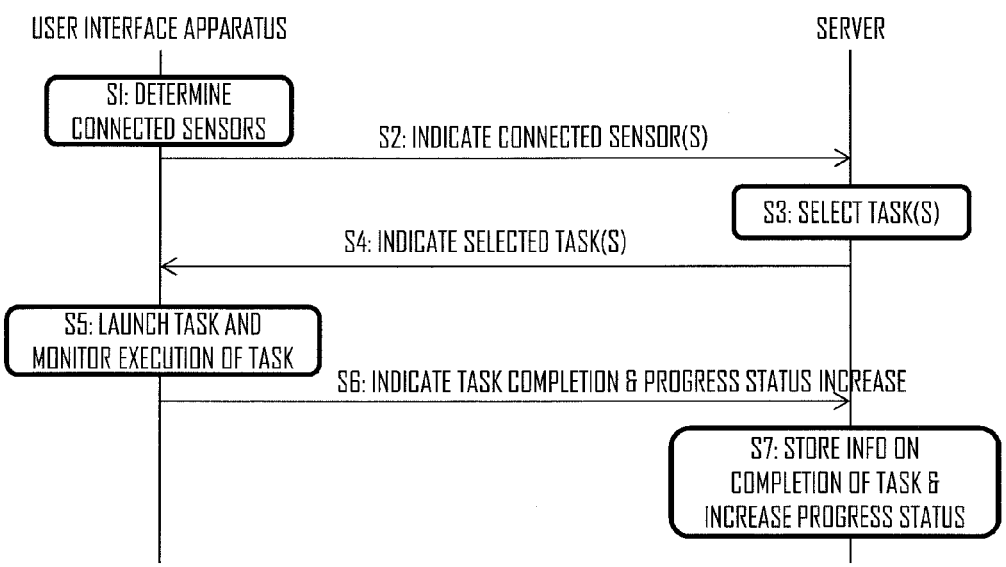
FIG. 10 illustrates an embodiment of operation of the processing system of FIG. 9.

FIG. 9 illustrates an embodiment where the operations of the processor 100 are distributed to a plurality of apparatuses that are in communication with each other over a network 904. The network 904 may comprise a public network such as the Internet, for example. This type of processing system may comprise the user interface apparatus 802 that may be any one of the above-mentioned personal electronic devices. The user interface apparatus 802 may have a communication connection with a server 902 comprising the memory 120 storing the tasks. The server 902 may also comprise the task selection module 106. Let us now consider an embodiment of a process in which the above-described functionality is distributed between the user interface apparatus 102 and the server 902 with reference to a diagram of FIG. 10. Referring to FIG. 10, the user interface apparatus 102 may determine in S1 the sensors connected to the user interface apparatus 102 or, in general, determine limitations to the tasks that may be currently carried out. In S2, the user interface apparatus transmits information on such limitations to the server 902. The server 902 then uses this information as an input to the task selection in S3. Other inputs may be used as well or instead, e.g. user input from the user or from a training coach of the user. The server may select one task or a plurality of tasks for the user to select. When the server 902 has selected the task(s), it indicates the selected task(s) to the user interface apparatus 102 in S4. The server may also indicate any target values associated with the task(s), as determined according to the progress status of the user, for example. In S5, the user interface apparatus launches one of the tasks, presents to the user appropriate target values and instructions as how to carry out the physical exercise(s) of the task, and monitors the execution of the task. Upon ending the task, the user interface apparatus 102 may transmit to the server 902 an indication about the completion of the task, e.g. fail or success. When the server 902 provided a plurality of tasks for the user to select in S4, the user interface apparatus 102 may indicate in S6 the task that was actually selected. If the task was completed and the raised progress status was also triggered, the corresponding information may also be provided in S6. The user interface apparatus may also provide any measurement data accumulated during the exercise in S6 so that the measurement information may be stored in the server for later analysis. In S7, the server 902 may store the information received in S6 in the memory 120 and update any necessary information in the memory, e.g. the task completion and/or the increase in the progress status.

Bearing in mind the modern high-speed data connections in communication networks, it should be appreciated that the distribution of the functionalities between the user interface apparatus 102 and the server 902 may be carried in a practically arbitrary manner. For example, the performance evaluation module 108 may also be included in the server, and the user interface apparatus 102 may stream the measurement data to the server 902 for analysis. Alternatively, some functions of the task selection module 106 and/or the performance evaluation module 108 may be carried out in the user interface apparatus 102, while other functions of the task selection module 106 and/or the performance evaluation module 108 may be carried out in the server 902. Therefore, it should be appreciated that the concept of the present invention may be carried out in a processing system comprising at least one apparatus configured to carry out any one of the above-described embodiments. The processing system may be comprised the apparatus of FIG. 1, the user interface apparatus 802 of FIG. 8, or the server 902. In other embodiments, the processing system is a system comprising a plurality of apparatuses such as the user interface apparatus 802 and the server 902, as described in connection with FIGS. 9 and 10.

As used in this application, the term 'circuitry' refers to all of the following: (a) hardware-only circuit implementations such as implementations in only analog and/or digital circuitry; (b) combinations of circuits and software and/or firmware, such as (as applicable): (i) a combination of processor(s) or processor cores; or (ii) portions of processor(s)/software including digital signal processor(s), software, and at least one memory that work together to cause an apparatus to perform specific functions; and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term "circuitry" would also cover an implementation of merely a processor (or multiple processors) or portion of a processor, e.g. one core of a multi-core processor, and its (or their) accompanying software and/or firmware. The term "circuitry" would also cover, for example and if applicable to the particular element, a baseband integrated circuit or applications processor integrated circuit (ASIC) for the apparatus according to an embodiment of the invention.

The processes or methods described in FIGS. 2 to 7 may also be carried out in the form of a computer process defined by a computer program. The computer program may be in source code form, object code form, or in some intermediate form, and it may be stored in some sort of carrier, which may be any entity or device capable of carrying the program. Such carriers include transitory and/or non-transitory computer media, e.g. a record medium, computer memory, read-only memory, electrical carrier signal, telecommunications signal, and software distribution package. Depending on the processing power needed, the computer program may be executed in a single electronic digital processing unit or it may be distributed amongst a number of processing units.

It will be obvious to a person skilled in the art that, as technology advances, the inventive concept can be implemented in various ways. The invention and its embodiments are not limited to the examples described above but may vary within the scope of the claims.

What is claimed is:

1. A personal training device that monitors a user's progress status in relation to at least one target value associated with physical exercise and outputs an instruction to the user regarding attaining the at least one target value, the personal training device comprising:
    at least one memory device storing a set of tasks, wherein each task defines the physical exercise and the at least one target value for the physical exercise, wherein the tasks are divided into a plurality of categories in an order of increasing training requirements, each category being associated with a plurality of tasks, and wherein each category is linked to a unique progress status indicator representing the training requirements; and
    at least one processing circuitry, wherein the at least one memory device and the at least one processing circuitry are configured to cause the personal training device to perform operations comprising:
        determining the progress status of the user,
        determining whether a sensor is currently connected to the processing circuitry to determine a type of measurement data the processing system is currently able to acquire;
        retrieving from the memory device at least one task from a category associated with a progress status indicator corresponding to said progress status of the user, the retrieved at least one task being selected based on a criterion, the criterion requiring that the selected at least one task have a target value measurable using the sensor that was determined to be currently connected to the processing circuitry, wherein said selection based on the criterion comprises excluding at least one task of the set of tasks that has a target value measurable with no sensor currently connected to the processing circuitry;
        outputting an instruction to the user to perform the retrieved at least one task;
        acquiring measurement data generated during said physical exercise using the sensor that was determined to be currently connected to the processing circuitry;
        comparing information acquired from the measurement data with the at least one target value associated with the instructed physical exercise;
        upon determining on the basis of the comparison that the user has reached the at least one target value, storing in the memory device a task indicator to indicate that the task has been completed;
        determining that the progress status of the user has increased sufficiently as a result of completing the task;
        increasing the progress status of the user; and
        outputting the progress status to the user.

2. The personal training device of claim 1, wherein the memory device stores a plurality of tasks for each category, and wherein the apparatus is configured to raise the progress status of the user when a plurality of tasks associated with the current progress status have been completed.

3. The personal training device of claim 2, wherein the at least one memory device and the at least one processing circuitry are configured to cause the apparatus to perform operations comprising:
    retrieving from the memory device the plurality of tasks from the category associated with said determined progress status of the user and presenting the tasks to the user via a user interface;
    receiving a user input indicating selection of one of the plurality of tasks presented to the user;
    providing the user with instructions and the at least one target value related the task through the user interface.

4. The personal training device of claim 1, wherein the at least one memory device and the at least one processing circuitry are configured to cause the processing system to eliminate from the selection at least one task for which no valid measurement data is available.

5. The personal training device of claim 1, wherein the processing system is configured to randomly select the task or tasks of a subset to be retrieved from the memory device.

6. The personal training device of claim 1, wherein at least one of the tasks comprises a plurality of physical exercises and at least one target value for each of the plurality of exercises.

7. The personal training device of claim 6, wherein the plurality of physical exercises comprised in the same task relate to different physical exercise types.

8. The personal training device of claim 1, wherein the at least one memory device and the at least one processing circuitry are configured to cause the processing system to perform operations comprising:

determining whether or not the measurement data indicates that at least one target value of the physical exercise has been exceeded by a determined amount during the physical exercise; and upon determining that the at least one target value has been exceeded by the determined amount, raising the progress status of the user by at least two categories.

9. The personal training device of claim 1, wherein the at least one memory device and the at least one processing circuitry are configured to cause the processing system to determine that the user has not completed one or more tasks on the current progress status of the user within a determined time period and, as a result, lower the progress status of the user and store the lowered progress status of the user in the memory device.

10. The personal training device of claim 1, wherein the set of tasks define at least one of the following physical exercises: walking, running, cycling, swimming, skiing, losing calories in a user-selectable activity, raising heart rate in a user-selectable activity, play a determined sports type, carrying out a fitness test, and resting.

11. The personal training device of claim 1, wherein the training requirements are increased between categories according to at least one of the following options: increasing a duration of the physical exercise, increasing the distance of the physical exercise, increasing heart rate requirements of the physical exercise, increasing the number of physical exercises included in a task, increasing the amount of calories to lose during the physical exercise, increasing training intensity of the physical exercise by reducing the time in which the user has to carry out the physical exercise, increasing the number of tasks that has to be completed before increasing the progress status, and increasing the number of physical exercises that must be carried out discontinuously to complete a task.

* * * * *

UNITED STATES PATENT AND TRADEMARK OFFICE
CERTIFICATE OF CORRECTION

| | | |
|---|---|---|
| PATENT NO. | : 9,433,823 B2 | |
| APPLICATION NO. | : 13/756767 | |
| DATED | : September 6, 2016 | |
| INVENTOR(S) | : Mika Erkkila | |

It is certified that error appears in the above-identified patent and that said Letters Patent is hereby corrected as shown below:

In the Specification

Column 1, Line 27:
Now reads: "provided a processing system processing system"
Should read: -- provided a processing system --

Column 2, Line 56:
Now reads: "may be determined be reading"
Should read: -- may be determined by reading --

Column 4, Line 12:
Now reads: "which may characterized in"
Should read: -- which may be characterized in --

Column 4, Line 14:
Now reads: "may also be expressed in or MET (Metabolic Equivalent of Task) unit the MET"
Should read: -- may also be expressed in MET (Metabolic Equivalent of Task) unit. The MET --

Column 5, Line 46:
Now reads: "by using at least on accelerometer"
Should read: -- by using at least one accelerometer --

Column 6, Line 13:
Now reads: "and no limiting this embodiment."
Should read: -- and not limiting this embodiment. --

Signed and Sealed this
Twenty-fifth Day of July, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,433,823 B2

Column 10, Line 65:
    Now reads: "system may be comprised the apparatus of"
    Should read: -- system may be comprised of the apparatus of Figure 1 --